(12) United States Patent
Kallem et al.

(10) Patent No.: US 9,314,447 B2
(45) Date of Patent: Apr. 19, 2016

(54) REDUCED DOSE PHARMACEUTICAL COMPOSITIONS OF FENOFIBRATE

(71) Applicant: Lupin Atlantis Holdings, S.A., Schaffhausen (CH)

(72) Inventors: Venkat Reddy Kallem, Hyderabad (IN); Raghu Rami Reddy Kasu, Maharashtra (IN); Subhasis Das, Maharashtra (IN); Vijaya Kumar Thommandru, Maharashtra (IN)

(73) Assignee: Lupin Atlantis Holdings, S.A., Schaffhausen (CH)

( * ) Notice: Subject to any disclaimer, the term of this patent is extended or adjusted under 35 U.S.C. 154(b) by 60 days.

(21) Appl. No.: 13/854,389

(22) Filed: Apr. 1, 2013

(65) Prior Publication Data

US 2014/0161881 A1 Jun. 12, 2014

(30) Foreign Application Priority Data

Dec. 11, 2012 (IN) .......................... 1397/KOL/2012

(51) Int. Cl.
| | |
|---|---|
| *A61K 9/14* | (2006.01) |
| *A61K 31/235* | (2006.01) |
| *A61K 31/216* | (2006.01) |
| *A61K 9/16* | (2006.01) |
| *A61K 9/50* | (2006.01) |

(52) U.S. Cl.
CPC .............. *A61K 31/235* (2013.01); *A61K 9/167* (2013.01); *A61K 9/5084* (2013.01); *A61K 31/216* (2013.01)

(58) Field of Classification Search
CPC combination set(s) only.
See application file for complete search history.

(56) References Cited

U.S. PATENT DOCUMENTS

| | | | |
|---|---|---|---|
| 4,895,726 A | 1/1990 | Curtet et al. | |
| 5,145,684 A | 9/1992 | Liversidge et al. | |
| 5,880,148 A | 3/1999 | Edgar et al. | |
| 6,027,747 A | 2/2000 | Terracol et al. | |
| 6,074,670 A | 6/2000 | Stamm et al. | |
| 6,277,405 B1 | 8/2001 | Stamm et al. | |
| 6,368,620 B2 | 4/2002 | Liu et al. | |
| 6,375,986 B1 | 4/2002 | Ryde et al. | |
| 6,531,158 B1 | 3/2003 | Teng et al. | |
| 6,589,552 B2 | 7/2003 | Stamm et al. | |
| 6,592,903 B2 | 7/2003 | Ryde et al. | |
| 6,652,881 B2 | 11/2003 | Stamm et al. | |
| 6,828,334 B2 | 12/2004 | Gidwani et al. | |
| 6,969,529 B2 | 11/2005 | Bosch et al. | |
| 7,037,529 B2 | 5/2006 | Stamm et al. | |
| 7,041,319 B2 | 5/2006 | Stamm et al. | |
| 7,101,574 B1 | 9/2006 | Criere et al. | |
| 7,189,412 B2 | 3/2007 | Okamoto | |
| 7,276,249 B2 | 10/2007 | Ryde et al. | |
| 7,320,802 B2 | 1/2008 | Ryde et al. | |
| 7,658,944 B2 | 2/2010 | Holm et al. | |
| 7,863,331 B2 | 1/2011 | Criere et al. | |
| 7,927,627 B2 | 4/2011 | Ryde et al. | |
| 7,976,869 B2 | 7/2011 | Blouquin et al. | |
| 2003/0138496 A1 | 7/2003 | Teng et al. | |
| 2004/0057998 A1 | 3/2004 | Stamm et al. | |
| 2004/0057999 A1 | 3/2004 | Stamm et al. | |
| 2004/0087656 A1 | 5/2004 | Ryde et al. | |
| 2006/0222706 A1 | 10/2006 | Flashner-Barak et al. | |
| 2006/0222707 A1 | 10/2006 | Lerner et al. | |
| 2007/0014846 A1 | 1/2007 | Holm et al. | |
| 2007/0071812 A1 | 3/2007 | Criere et al. | |
| 2007/0264348 A1 | 11/2007 | Ryde et al. | |
| 2007/0264349 A1* | 11/2007 | Lee et al. ...................... 424/489 |
| 2007/0298115 A1 | 12/2007 | Ryde et al. | |
| 2008/0138424 A1 | 6/2008 | Ryde et al. | |
| 2008/0241070 A1 | 10/2008 | Ryde et al. | |
| 2008/0248101 A1 | 10/2008 | Criere et al. | |
| 2009/0035379 A1 | 2/2009 | Stamm et al. | |
| 2010/0112049 A1 | 5/2010 | Criere et al. | |
| 2011/0159082 A1 | 6/2011 | Criere et al. | |
| 2011/0311619 A1 | 12/2011 | Herry et al. | |
| 2013/0115246 A1 | 5/2013 | Kallem et al. | |

FOREIGN PATENT DOCUMENTS

| | | |
|---|---|---|
| WO | 2006/037348 A1 | 4/2006 |
| WO | WO 2010/082214 A2 | 7/2010 |

OTHER PUBLICATIONS

Bawa, "Nanopharmaceuticals for Drug Delivery—A Review," *Touch Briefings*, vol. 6, pp. 122-127 (2009).
Gülsün et al., "Nanocrystal Technology for Oral Delivery of Poorly Water-Soluble Drugs," *Fabad J. Pharm. Sci.*, vol. 34, pp. 55-65 (2009).
Jain et al., "Solubility Enhancement Techniques With Special Emphasis on Hydrotrophy," *International Journal of Pharma Professional's Research*, vol. 1, No. 1, pp. 34-45 (Jul. 2010).
Junghanns, Jens-Uwe A.H., et al., "Nanocrystal technology, drug delivery and clinical applications," *International Journal of Nanomedicine*, vol. 3, No. 3, pp. 295-309 (2008).
Lofibra® [Fenofibrate capsules (micronized)], Drug Leaflet, Novopharm Limited, Manufactured for: Gate Pharmaceuticals—Div. of Teva Pharmaceuticals USA, Sellersville, PA 18960 (Jul. 2003), 2 pp.
Lofibra® (fenofibrate tablets) 54 mg and 160 mg, Drug Leaflet, 1p. (Jan. 2010).
MJR Pharmjet GMBH, "Innovative nanosized oral drug-delivery system of fenofibrate with superior properties by using microjet reactor technology," 7 pp. (2011).

* cited by examiner

*Primary Examiner* — Ileana Popa
*Assistant Examiner* — Nicole Babson
(74) *Attorney, Agent, or Firm* — Leydig, Voit & Mayer, Ltd.

(57) ABSTRACT

The present invention provides a reduced dose oral pharmaceutical composition comprising mixture of nanoparticulate fenofibrate and micronized fenofibrate and one or more pharmaceutically acceptable excipients.

6 Claims, 2 Drawing Sheets

REDUCED DOSE PHARMACEUTICAL COMPOSITIONS OF FENOFIBRATE

CROSS REFERENCE TO RELATED APPLICATION

This application claims benefit of Application No. 1397/KOL/2012, filed 11 Dec. 2012 in India and which application is incorporated herein by reference. A claim of priority to all, to the extent appropriate, is made.

FIELD OF THE INVENTION

The invention relates to a reduced dose oral pharmaceutical composition of fenofibrate which exhibits substantial bioequivalence to Antara® Capsules under fasting condition and is substantially free of food effect. The invention provides a method of treatment of hyperlipidemias, hypercholesterolemias and/or hypertriglyceridemias in a patient by administering reduced dose oral pharmaceutical composition of fenofibrate with or without food and a process of manufacturing the composition.

BACKGROUND OF THE INVENTION

Fibrates are lipid regulating agents. Examples of fibrates include fenofibrate, bezafibrate, clofibrate and ciprofibrate. The compounds are regarded as prodrugs and are metabolised in vivo to their active metabolites. For illustrative purposes only, the following is based on a specific example of a fibrate, namely fenofibrate. Fenofibrate is chemically named as 2-[4-(4-chlorobenzoyl) phenoxy]-2-methyl-propanoic acid, 1-methylethyl ester. Fenofibrate is metabolised to the active substance fenofibric acid. Fenofibric acid has an elimination half-life of about 20 hours.

Fenofibric acid is the active metabolite of fenofibrate which leads to reduction in total cholesterol, LDL cholesterol, apolipoprotein B, total triglycerides, and triglyceride rich lipoprotein (VLDL) in treated patients. In addition, treatment with fenofibrate results in increased high density lipoprotein (HDL) and apoproteins apo AI and apo AII. Fenofibrate acts as a potent lipid regulating agent offering unique and clinical advantages over existing products in the fibrate family of drug substances. Fenofibrate produces substantial reduction in plasma triglyceride levels in hypertriglyceridemic patients and in plasma cholesterol and LDL-C in hypercholesterolemic and mixed dyslipidemic patients. Clinical studies have demonstrated that elevated levels of total cholesterol, low density lipoprotein cholesterol (LDL-C), and apo-lipoprotein B (apo B) are associated with human atherosclerosis. Decreased levels of high density lipoprotein cholesterol (HDL-C) and its transport complex, apolipoprotein A (apo AI and apo AII) are associated with the development of atherosclerosis. Fenofibrate is also effective in the treatment of Diabetes Type II and metabolic syndrome. Fenofibrate is also indicated as adjunctive therapy to diet for treatment of adult patients with hypertriglyceridemia (Fredrickson Types IV and V hyperlipedemia).

Fibrates are drug substances known to be poorly and variably absorbed after oral administration. Normally fibrates are prescribed to be taken with food in order to increase the bioavailability. Fenofibrate is very poorly soluble in water, and the absorption of which in the digestive tract is limited. An increase in its solubility or in its rate of solubilization leads to better digestive absorption. Therefore a number of improvements have been made in an effort to improve the bioavailability and efficacy of currently approved fenofibrate dosage forms. Various approaches such as micronization of the fenofibrate, addition of a surfactant, and co-micronization of fenofibrate with a surfactant have been explored in order to increase the rate of solubilization of fenofibrate.

U.S. Pat. No. 5,145,684 discloses nanoparticles of drug substances including lipid regulating agents having non-crosslinked surface modifier.

U.S. Pat. Nos. 6,375,986; 6,969,529; 7,320,802; 7,276,249; 7,927,627; 6,592,903 and US patent applications 2004/0087656; 2008/0241070; 2008/0138424 and 2007/0264348 disclose nanoparticulate compositions of fenofibrate.

U.S. Pat. Nos. 6,277,405; 6,074,670; 6,652,881; 7,037,529; 7,041,319; 6,589,552; 6,531,158; 7,101,574 and 7,863,331 and US patent applications 2004/0057998; 2007/0071812; 2008/0248101; 2011/0159082; 2010/0112049 and 2009/0035379 describe micronized fenofibrate compositions.

U.S. Pat. Nos. 4,895,726; 5,880,148 and 7,189,412 describe composition wherein fenofibrate is co-micronized with the surface-active agents.

U.S. Pat. No. 7,658,944 discloses tablet composition of fenofibrate with PEG and Poloxamer. U.S. Pat. No. 7,976,869 discloses fenofibrate tablet and granules comprising micronized fenofibrate, polyvinylpyrrolidone, and pregelatinised starch.

U.S. Pat. No. 6,828,334 discloses inclusion complex of fenofibrate with cyclodextrins.

U.S. Pat. No. 6,027,747 discloses solid dispersion of fenofibrate.

US 2006/0222706 and US 2006/0222707 describe fenofibrate in intimate association with menthol and surfactant active agents which provides much enhanced bioavailability of fenofibrate.

U.S. Pat. No. 6,531,158 and US 2003/0138496 disclose composition of micronized fenofibrate with inert hydro soluble carriers.

WO 2010/082214 discloses a fenofibrate formulation with enhanced oral bioavailability comprising fenofibrate dissolved in a lipophilic surfactant. It also discloses that such formulation at lower doses may improve side effect profile.

US 2007/0014846 discloses compositions, particularly, pharmaceutical compositions in particulate form such as granulate or in solid dosage forms comprising a combination of a fibrate and a statin. More specifically, it discloses a solid pharmaceutical composition comprising atorvastatin and a low dose, i.e. a reduced amount, of fenofibrate having improved bioavailability and/or improved pharmacological response, i.e. improved effect.

US 2004/0057999 discloses an orally administrable fenofibrate tablet, wherein the required daily dose is lower than 200 mg.

Micronization of the drug and the addition of surface active agents have raised the bioavailability of fenofibrate thereby allowing the amount of drug dose to be reduced from 100 mg per dose to 67 mg per dose and then subsequently to 54 mg per dose, all with the same bioavailability in the fed state. Similarly the nanoparticle formulations of the drug have further allowed the reduction of the dose to 48 mg per dose with the bioavailability of the "fasted state" being reported as similar to the fed state. Further, the applicants have found that the composition comprising nanoparticulate fenofibrate at reduced doses imposes bioequivalence problems when compared with Antara® Capsule containing micronized fenofibrate under fasting condition.

The above disclosed prior arts direct various fenofibrate compositions wherein fenofibrate is present either in nanoparticle or in micronized form. None of the prior arts discloses the use of mixture of nanoparticulate fenofibrate and micronized fenofibrate that too for the reduced dose oral pharmaceutical composition of fenofibrate. The applicants surprisingly found that these compositions can be made bioequivalent to Antara® capsules under fasting condition by appropriate selection of the particle size of fenofibrate. The compositions of the invention are also substantially free of food effect.

Thus the present invention relates to a reduced dose oral pharmaceutical composition of fenofibrate comprising mixture of nanoparticulate fenofibrate and micronized fenofibrate which exhibits substantial bioequivalence to Antara® Capsules under fasting condition and is substantially free of food effect. Further, the reduced dose oral pharmaceutical composition of the present invention offers advantages such as (1) smaller doses of drug required to obtain the same pharmacological effect; (2) smaller tablet or capsule or other smaller solid dosage form in size (3) substantially similar pharmacokinetic profiles of fenofibrate composition when administered in the fed and the fasted state (4) reduction of side-effects associated with higher doses.

SUMMARY OF THE INVENTION

The present invention relates to a reduced dose oral pharmaceutical composition of fenofibrate.

An embodiment of the invention relates to a reduced dose oral pharmaceutical composition comprising fenofibrate, wherein the composition comprises mixture of nanoparticulate fenofibrate and micronized fenofibrate and one or more pharmaceutically acceptable excipients.

Yet another embodiment discloses a reduced dose oral pharmaceutical composition comprising fenofibrate, wherein the composition comprises mixture of nanoparticulate fenofibrate and micronized fenofibrate and one or more pharmaceutically acceptable excipients which exhibits bioequivalence to Antara® Capsules under fasting condition wherein the bioequivalence of the composition is established by: (i) a 90% Confidence Interval for AUC which is between 0.80 and 1.25; and (ii) a 90% Confidence Interval for Cmax, which is between 0.80 and 1.25.

Yet another embodiment of the invention directs a reduced dose oral pharmaceutical composition comprising fenofibrate, wherein the composition comprises mixture of nanoparticulate fenofibrate and micronized fenofibrate and one or more pharmaceutically acceptable excipients wherein the composition is substantially free of food effect when administered to a human.

Another embodiment of the invention encompasses an oral pharmaceutical composition comprising about 90 mg of fenofibrate wherein the composition comprises mixture of nanoparticulate fenofibrate and micronized fenofibrate and one or more pharmaceutically acceptable excipients.

Another embodiment of the invention encompasses an oral pharmaceutical composition comprising about 30 mg of fenofibrate wherein the composition comprises mixture of nanoparticulate fenofibrate and micronized fenofibrate and one or more pharmaceutically acceptable excipients.

Yet another embodiment discloses an oral pharmaceutical composition comprising about 90 mg of fenofibrate wherein the composition comprises mixture of nanoparticulate fenofibrate and micronized fenofibrate and one or more pharmaceutically acceptable excipients, wherein the composition exhibits a least square mean of $AUC_{(0-t)}$ about 119.8507 mcg·h/ml under fasting condition and a least square mean of $AUC_{(0-t)}$ about 134.1769 mcg·h/ml under fed condition.

Yet another embodiment discloses an oral pharmaceutical composition comprising about 90 mg of fenofibrate wherein the composition comprises mixture of nanoparticulate fenofibrate and micronized fenofibrate and one or more pharmaceutically acceptable excipients, wherein the composition exhibits a least square mean of $C_{max}$ about 4.7915 mcg/ml under fasting condition and a least square mean of $C_{max}$ about 5.5899 mcg/ml under fed condition.

Yet another embodiment discloses a method of treating a patient in need of treatment for primary hyperlipidemias, hypercholesterolemias and/or hypertriglyceridemias comprising administering to the patient reduced dose oral pharmaceutical composition of fenofibrate.

DETAILED DESCRIPTION OF THE INVENTION

Figure 1:
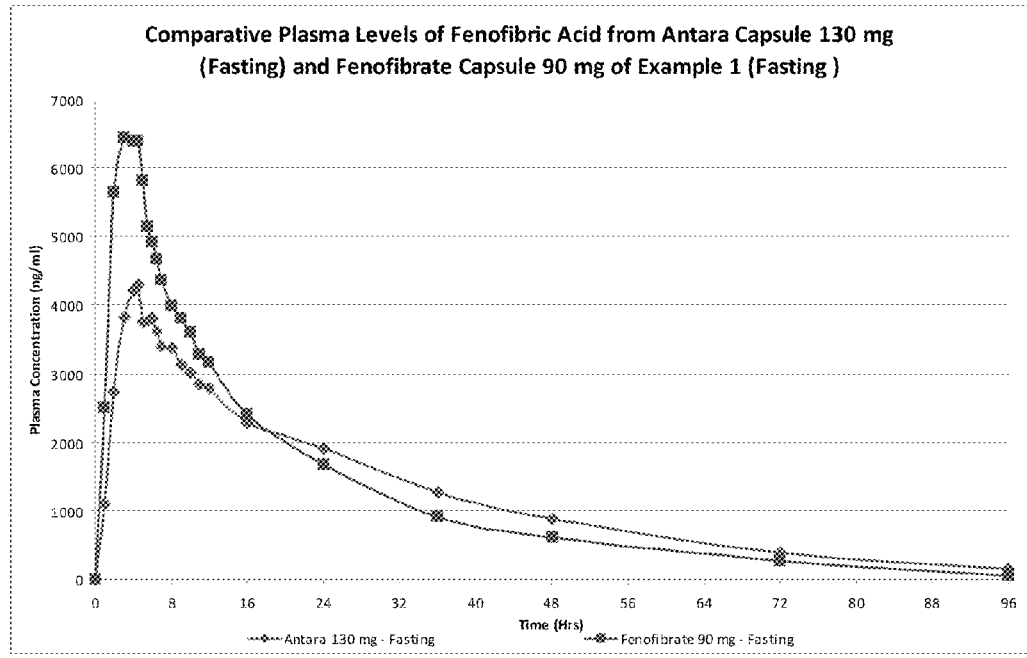
FIG. 1: Represents the comparative plasma level of fenofibric acid of Antara® 130 mg capsule and nanoparticulate fenofibrate composition of Example 1 under fasting condition.
Figure 2:
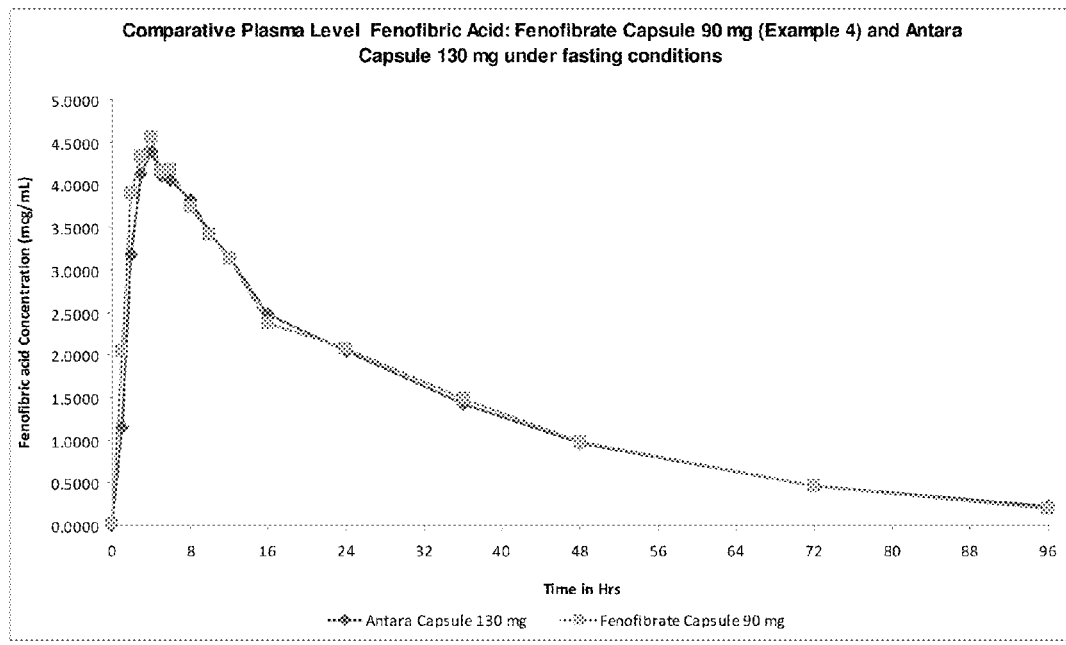
FIG. 2: Represents the comparative plasma level of fenofibric acid of Antara® 130 mg capsule and fenofibrate composition of Example 4 under fasting condition.
Figure 3:
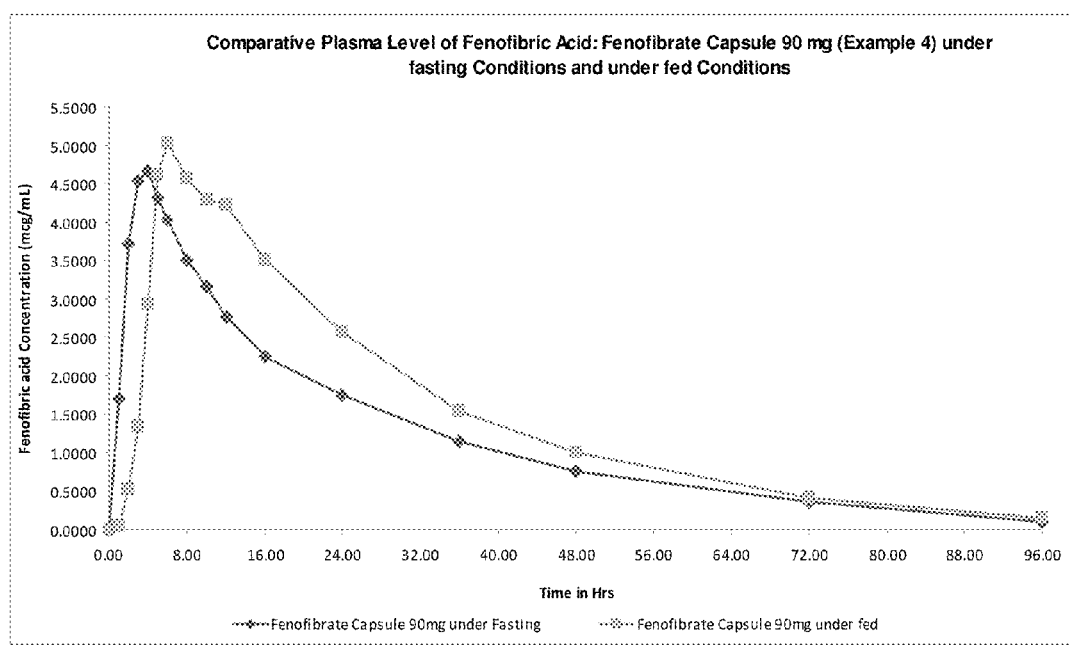
FIG. 3: Represents the comparative plasma level of fenofibric acid of fenofibrate composition of Example 4 under fasting and fed condition.

The specification discloses a reduced dose oral pharmaceutical composition of fenofibrate.

The specification further discloses a reduced dose oral pharmaceutical composition comprising fenofibrate, wherein the composition comprises mixture of nanoparticulate fenofibrate and micronized fenofibrate and one or more pharmaceutically acceptable excipients.

The composition of the invention exhibits substantial bioequivalence to Antara® Capsules under fasting condition. The composition of the invention also relates to a reduced dose oral pharmaceutical composition comprising fenofibrate, wherein the composition comprises mixture of nanoparticulate fenofibrate and micronized fenofibrate and one or more pharmaceutically acceptable excipients wherein the composition is substantially free of food effect when administered to a human. The composition makes it effective at lower doses as well as improves high dose associated side effect profile of fenofibrate. The composition also offers a method of treatment of primary hyperlipidemias, hypercholesterolemias and/or hypertriglyceridemias comprising administering reduced dose oral pharmaceutical composition of fenofibrate to the patient with or without food. The specification discloses a process of manufacturing reduced dose oral pharmaceutical compositions comprising a mixture of nanoparticulate fenofibrate and micronized fenofibrate and one or more pharmaceutically acceptable excipients.

"Fenofibrate" as employed herein refers to fenofibrate, its derivatives, prodrugs, active metabolites, and/or its polymorphs, solvates, hydrates, enantiomers, racemates and mixtures thereof. Further, it also includes amorphous or crystalline polymorphic forms of fenofibrate, and mixtures thereof. Fenofibrate for the purpose of the invention is used as a mixture of micronized form and nanoparticulate form.

The term "mixture" refers generally to a system having one or more component which are mixed but not combined chemically. The mixture of one component contains a single component having different physical properties such as different concentration and different particle size. The mixture may be physical combination of one or more components on which the identities are retained and are mixed in the form of alloys, solutions, suspensions and colloids.

The mixture of nanoparticulate fenofibrate and micronized fenofibrate of the invention comprises a ratio of nanoparticulate fenofibrate to micronized fenofibrate ranging from 90:10 to 10:90 wt/wt. The mixture of nanoparticulate fenofibrate and micronized fenofibrate of the invention has a ratio of nanoparticulate fenofibrate to micronized fenofibrate ranging preferably from 75:25 to 25:75 wt/wt, more preferably from 60:40 to 40:60 wt/wt and the most preferable ratio is 50:50 wt/wt.

The mixture of nanoparticulate and micronized fenofibrate may substantially be present in solution and suspension form, preferably in suspension form.

The nanoparticulate fenofibrate, particles may have particle size of less than about 1000 nm. The term "nanoparticulate fenofibrate" is meant to have effective particle size of less than about 1000 nm. The term "effective particle size" in context of nanoparticulate fenofibrate is meant that the 90% of the particles have a particle size less than about 1000 nm and preferably less than about 900 nm. The micronized fenofibrate, particles may have particle size of less than about 60 μm. The term "micronized fenofibrate" is meant to have effective particle size of less than about 60 μm. The term "effective particle size" in context of micronized fenofibrate is meant that the 90% of the particles have a particle size less than about 60 μm and preferably less than about 50 μm.

The USFDA has approved fenofibrate tablet as well as capsule which contain different doses of fenofibrate. Lipidil® Capsule of Abbott contained 100 mg of fenofibrate. Tricor Micronised® Capsule of Abbott contained 67, 134 and 200 mg of fenofibrate. Tricor® Tablet of Abbott contained 54 and 160 mg of fenofibrate. The above mentioned dosage forms have been discontinued by Abbott. The prescription dosage form of fenofibrate such as Tricor® Tablet of Abbott contains 48 and 145 mg, Lipophen® Capsule of Cipher contains 50, 100 and 150 mg, Triglide® Tablet of Skyepharma contains 50 and 160 mg, Fenoglide® Tablet of Sciele Pharma contains 40 and 120 mg, Antara® Capsule of Lupin Atlantis contains 43 and 130 mg of fenofibrate.

In general, it is known that the absorption and bioavailability of drug substance can be affected by a variety of factors when administered orally. Such factors include the presence of food in the gastrointestinal tract and, in general, the gastric residence time of a drug substance is significantly longer in the presence of food than in the fasted state. If the bioavailability of a drug substance is affected beyond a certain point due to the presence of food in the gastrointestinal tract, the drug substance is said to exhibit a food effect. Food effects are important because there is a risk associated with administering the drug substance to a patient. The risk derives from the potential that absorption into the bloodstream may be adversely affected to the point that the patient risks insufficient absorption to remedy the condition for which the drug was administered. The pharmacokinetic studies of Antara® Capsule discloses that the extent of absorption of fenofibric acid was unaffected when Antara® was taken either in fasted state or with a low-fat meal. However, the Cmax of Antara® increases in the presence of a low-fat meal. $T_{max}$ was unaffected in the presence of a low-fat meal. In the presence of a high-fat meal, there was a 26% increase in AUC and 108% increase in $C_{max}$ of fenofibric acid from Antara® relative to fasting state.

The applicants have found that administration of a 90 mg nanoparticulate fenofibrate capsule in a fasted state is not bioequivalent to a 130 mg fenofibrate capsule (Antara®) which contains micronized fenofibrate. The composition containing 90 mg nanoparticulate fenofibrate exhibits about 63% increase in Cmax when compared to Antara Capsules under fasting state. The non-bioequivalence is significant because it means that the nanoparticulate fenofibrate dosage form exhibits significantly greater drug absorption. For the nanoparticulate dosage form containing 90 mg fenofibrate to be bioequivalent to the Antara® capsule which contains micronized fenofibrate under fasting condition, it becomes critical to select the particle size of fenofibrate in order to meet the bioequivalence criteria for the reduced dose oral pharmaceutical composition of fenofibrate.

Accordingly an embodiment of the present invention provides a reduced dose pharmaceutical composition comprising fenofibrate, wherein the composition comprises a mixture of nanoparticulate fenofibrate and micronized fenofibrate and one or more pharmaceutically acceptable excipients wherein the composition is bioequivalent to Antara® capsule and the bioequivalence is established by: (i) a 90% Confidence Interval for AUC which is between 0.80 and 1.25; and (ii) a 90% Confidence Interval for Cmax, which is between 0.80 and 1.25.

Another embodiment of the present invention provides a reduced dose oral pharmaceutical composition comprising fenofibrate, wherein the composition comprises mixture of nanoparticulate fenofibrate and micronized fenofibrate and one or more pharmaceutically acceptable excipients, is substantially free of food effect when administered to a human.

The term "reduced dose" used herein refers to the low dose relative to Antara® 43 mg and 130 mg Capsule that is 30 mg and 90 mg of fenofibrate respectively.

As used herein, the term "bioequivalence" denotes a scientific basis on which two or more pharmaceutical compositions containing same active ingredient are compared with one another. "Bioequivalence" means the absence of a significant difference in the rate and extent to which the active agent in pharmaceutical equivalents or pharmaceutical alternatives becomes available at the site of action when administered in an appropriately designed study. Bioequivalence can be determined by an in vivo study comparing a pharmacokinetic parameter for the two compositions. Parameters often used in bioequivalence studies are Tmax, Cmax, $AUC_{0-inf}$, $AUC_{0-t}$. In the present context, substantial bioequivalence of two compositions is established by 90% confidence intervals (CI) of between 0.80 and 1.25 for AUC and Cmax.

The term "bioavailability" denotes the degree to which a drug substance becomes available to the target tissue after administration.

The term "substantially free of food effect" used herein refers to food effect which has no clinical significance. In the present context, a composition is substantially free of food effect if AUC and Cmax are in the range of ±30% of a specified value.

In a specific embodiment, substantial bioequivalence of the reduced dose oral pharmaceutical composition comprising fenofibrate, wherein the composition comprises mixture of nanoparticulate fenofibrate and micronized fenofibrate and one or more pharmaceutically acceptable excipients with Antara® Capsule under fasting condition is determined according to the Federal Drug Administration's (FDA) and the corresponding European regulatory agency (EMEA) guidelines and criteria.

The term "$T_{max}$" denotes the time to reach the maximal plasma concentration ($C_{max}$) after administration; $AUC_{0-inf}$ or AUC denotes the area under the plasma concentration versus time curve from time 0 to infinity; $AUC_{0-t}$ denotes the area under the plasma concentration versus time curve from time 0 to time t. For statistical analysis of pharmacokinetic data, the logarithmic transformed $AUC_{0-t}$, $AUC_{0-\infty}$, or $C_{max}$ data can be analyzed statistically using analysis of variance.

The terms "without food" and "fasted" are equivalent and are as given by FDA guidelines and criteria. The term "fasted" means the condition wherein no food is consumed within 1 hour prior to administration of the composition or 2 hours after administration of the composition.

As used herein, "about" refers to a range of values ±20% of a specified value.

Summary of Bioequivalence Studies

Study 1:

In a bioequivalence study the comparison of the relative bioavailability of 90 mg fenofibrate composition prepared according to example 1 and Antara® 130 mg Capsules was carried out in 12 healthy volunteers under fasted conditions.

In these examples, "fasted" is based on a 10-hour absence of food; however, a skilled artisan would know other methods of preparing fasted conditions. For example, "fasted" may be understood as 10 hour or more absence of food.

Conditions for fasted state were according to Guidance for Industry: Food-effect Bioavailability and Fed Bioequivalence Studies; CDER December 2002: An overnight fast of the subjects of at least 10 hours; no breakfast and no food intake 4 hours after drug administration; 240 ml plain water at study drug administration.

Results of bioequivalence studies of composition prepared according to example 1 and Antara® Capsule under fasting conditions is as indicated in the Table 1 below:

TABLE 1

Represents the results of bioequivalence studies of 90 mg fenofibrate composition prepared according to example 1 and Antara ® 130 mg Capsules under fasting conditions Results of Bioequivalence Studies Under Fasting Condition (N = 12)

| Fenofibrate 90 mg Capsule (Example 1) | | | Antara ® 130 mg Capsule | | |
|---|---|---|---|---|---|
| #$AUC_{0-t}$ (ng · h/ml) | #$C_{max}$ (ng/ml) | *$T_{max}$ (hours) | #$AUC_{0-t}$ (ng · h/ml) | #$C_{max}$ (ng/ml) | *$T_{max}$ (hours) |
| 114073.70 | 7326.84 | 3.00 | 113006.43 | 4480.10 | 4.50 |

Statistical Parameters

| Parameters | $C_{max}$ | $AUC_{0-t}$ |
|---|---|---|
| Least Square Mean Ratio (%) | 163.54 | 100.94 |
| 90% Confidence Interval | 145.93-183.26 | 95.50-106.69 |
| Intra-subject CV (%) | 16.24 | 7.86 |

Least square means
*Median

Study 2:

In another bioequivalence study the comparison of the relative bioavailability of 90 mg fenofibrate composition prepared according to example 4 and Antara® 130 mg Capsules was carried out in 36 healthy volunteers under fasted conditions.

Results of bioequivalence studies of composition prepared according to example 4 and Antara® Capsule under fasting conditions is as indicated in the Table 2 below:

TABLE 2

Represents the results of bioequivalence studies of 90 mg fenofibrate composition prepared according to example 4 and Antara ® 130 mg Capsules under fasting conditions Study 2 - Fasting Bioequivalence Study (N = 36)

| Fenofibrate 90 mg Capsule (Example 4) | | | Antara ® 130 mg Capsule | | |
|---|---|---|---|---|---|
| #$AUC_{0-t}$ (mcg · h/ml) | #$C_{max}$ (mcg/ml) | *$T_{max}$ (hours) | #$AUC_{0-t}$ (mcg · h/ml) | #$C_{max}$ (mcg/ml) | *$T_{max}$ (hours) |
| 119.8507 | 4.7915 | 3.00 | 115.0134 | 4.3490 | 4.00 |

Statistical Parameters

| Parameters | $C_{max}$ | $AUC_{0-t}$ |
|---|---|---|
| Least Square Mean Ratio (%) | 110.18 | 104.21 |
| 90% Confidence Interval | 102.27-118.69 | 99.03-109.65 |
| Intra-subject CV (%) | 18.68 | 12.79 |

Least square means
*Median

Study 3:

In the $3^{rd}$ study the effect of food on the bioavailability of oral pharmaceutical compositions containing 90 mg fenofibrate, prepared according to Example 4 was evaluated in 21 healthy volunteers.

Results of effect of food on the bioavailability of oral pharmaceutical compositions containing 90 mg fenofibrate, prepared according to Example 4 is as indicated in the Table 3 below:

TABLE 3

Represents the results effect of food on the bioavailability of oral pharmaceutical compositions containing 90 mg fenofibrate, prepared according to Example 4 using fasting and Fed condition (high fat breakfast - 952 Kcal).

Study 3 - Food Effect Study (N = 21)

| Fenofibrate 90 mg Capsule (Under Fasting Condition) | | | Fenofibrate 90 mg Capsule (Under Fed condition) | | |
|---|---|---|---|---|---|
| #$AUC_{0-t}$ (mcg · h/ml) | #$C_{max}$ (mcg/ml) | *$T_{max}$ (hours) | #$AUC_{0-t}$ (mcg · h/ml) | #$C_{max}$ (mcg/ml) | *$T_{max}$ (hours) |
| 105.8999 | 4.8459 | 3.00 | 134.1769 | 5.5899 | 6.00 |

Statistical Parameters

| Parameters | $C_{max}$ | $AUC_{0-t}$ |
|---|---|---|
| Least Square Mean Ratio (%) | 115.35 | 126.70 |
| 90% Confidence Interval | 103.90-128.06 | 120.31-133.43 |
| Intra-subject CV (%) | 19.59 | 9.70 |

Least square means
*Median

1. Results of Table 1 demonstrate that oral pharmaceutical composition containing 90 mg fenofibrate prepared according to Example 1 shows about 63% increase in $C_{max}$ compared to Antara® Capsules 130 mg under fasting condition.
2. Results of Table 2 demonstrate that oral pharmaceutical composition containing 90 mg fenofibrate prepared according to Example 4 shows bioequivalence to Antara® Capsules 130 mg under fasting condition.
3. Results of Table 2 demonstrate that oral pharmaceutical composition containing 90 mg fenofibrate prepared according to Example 4 shows no significant difference in $T_{max}$ compared to Antara® Capsule 130 mg under fasting condition.

4. Results of Table 3 demonstrate that oral pharmaceutical composition containing 90 mg fenofibrate prepared according to Example 4 has increase $C_{max}$ and $AUC_{0-t}$ to about 15.35% and 26.70%, respectively, under fed condition compared to fasting condition. However, the effect of food on bioavailability (both $AUC_{0-t}$ and $C_{max}$) of oral pharmaceutical composition containing 90 mg fenofibrate prepared according to Example 4 is found to be modest and is not of clinically significance.

5. The reduced dose oral pharmaceutical composition comprising fenofibrate, wherein the composition comprises mixture of nanoparticulate fenofibrate and micronized fenofibrate and one or more pharmaceutically acceptable excipients may be taken without regard to meals.

The reduced dose oral pharmaceutical composition includes, but not limited to granules, grains, beads or pellets, minitablets which are filled into capsules or sachets or are compressed to tablets by conventional methods. The granules, grains, beads or pellets are optionally enteric-coated or coated with a protective coating.

The term "pharmaceutically acceptable excipients" is intended to denote any material, which is inert in the sense that it substantially does not have any therapeutic and/or prophylactic effect. Such excipients may be added with the purpose of making it possible to obtain a pharmaceutical composition, which has acceptable technical properties.

Examples of suitable excipients for use in a composition according to the invention include but are not limited to fillers, diluents, binders, disintegrants, stabilizers, lubricants, antifoaming agents or mixtures thereof.

Fillers or diluents, which include, but are not limited to compressible sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like can be used. Filler or diluents can also function as inert carrier. The individual particle size of the inert carrier can be between 50 and 500 microns.

Binders include, but are not limited to hydrophilic polymers. The term "hydrophilic polymers" used herein mean any high molecular weight substance (greater, for example, than 300) having sufficient affinity towards water to dissolve therein and form a gel. Examples of such polymers are polyvinylpyrrolidone, poly (vinyl alcohol), hydroxypropylcellulose, hydroxymethylcellulose, hydroxypropylmethylcellulose (HPMC), gelatin, etc. Polymer blends are also suitable. The preferred hydrophilic polymer is HPMC. The HPMC used in this invention has, for example, a molecular weight comprised between 5000 and 60,000, preferably for example between 10,000 and 30,000.

Specific examples of disintegrants includes, but are not limited to alginic acid or alginates, microcrystalline cellulose, hydroxypropyl cellulose and other cellulose derivatives, croscarmellose sodium (Ac-di-sol), crospovidone, polacrillin potassium, sodium starch glycolate, starch, pregelatinized starch, carboxymethyl starch (e.g. Primogel® and Explotab®).

Glidants and lubricants include, but are not limited to stearic acid, magnesium stearate, calcium stearate or other metallic stearate, talc, waxes and glycerides, light mineral oil, polyethylene glycols, glyceryl behenate, colloidal silica, hydrogenated vegetable oils, sodium stearyl fumarate.

Stabilizers include but are not limited to, surface-active agents. Any surfactant is suitable, whether it be amphoteric, non-ionic, cationic or anionic. Examples of such surfactants are: sodium lauryl sulfate, monooleate, monolaurate, monopalmitate, monostearate or another ester of polyoxyethylene sorbitane, sodium dioctylsulfosuccinate (DOSS), lecithin, stearylic alcohol, cetostearylic alcohol, polyoxyethylene fatty acid glycerides, Poloxamer®, etc. Mixtures of surfactants are also suitable. The preferred surfactant is sodium laurylsulfate, which can be co-micronized with fenofibrate.

Antifoaming agents include, but are not limited to simethicone emulsion, dimethicone emulsion.

The reduce dose oral pharmaceutical composition may be prepared by any known technique in the art but not limited to wet granulation, melt granulation and dry granulation. The preferred method is wet granulation which includes low shear wet granulation; high shear wet granulation and fluid bed granulation. The most preferred method according to the invention uses the fluidized bed granulation principle. In particular, the invention employs the mixture of nanoparticulate and micronized fenofibrate. Fenofibrate of the total dose can be divided into two portions in order to achieve nanoparticulate and micronized fenofibrate. Fenofibrate portion reserved to make nanoparticles may be subjected to various processes such as wet milling, high-pressure homogenization, emulsification, precipitation, rapid expansion, and spray freezing to produce fenofibrate nanoparticles. The preferred method is wet milling using suitable mill such as DYNO mill.

The other portion can be micronized with suitable techniques to achieve particle size in micron range. Micronization may be a mechanical process that involves the application of force to a particle, thereby resulting in the break-up of the particle. Such force may be applied by collision of particles at high speeds. Micronization may be carried out, for example, by grinding, cad milling, air-jet micronizer, ball mill, or pin mill to produce micronized particles.

The size of a particle is determined by any of the methods commonly known in the art. The following methods, for example, may be used: sieves, sedimentation, electrozone sensing (coulter counter), microscopy, or Low Angle Laser Light Scattering (LALLS).

The micronized portion of fenofibrate is mixed with nanoparticulate suspension of remaining portion of fenofibrate. The nanoparticulate form of fenofibrate is in a solution of a hydrophilic polymer and, optionally, a surfactant and antifoaming agent. The final suspension containing fenofibrate in nanoparticulate and micronized form is sprayed onto the inert cores. For the purpose of making fenofibrate suspension, solvents like aqueous or organic (for example ethanol) can be used. Purified water is preferred.

The granules thus obtained can, if desired, be provided with a coating which can be lubricated and filled into hard gelatin capsule or can be compressed into tablets.

When the granules obtained (whether subsequently coated or not) is compressed to form tablets, this step can be implemented using any conventional technique which is suitable, for example using an alternating or rotating compressing equipment.

It must be noted that as used in the specification and the appended claims, the singular forms also include the plural unless the context clearly dictates otherwise.

The examples below are representation only and should not be construed to limit the scope of the invention.

Example 1

| Sr. No. | Ingredients | Qty (mg/cap) |
|---|---|---|
| 1 | Fenofibrate | 90.00 |
| 2 | Sodium lauryl sulphate | 5.40 |
| 3 | Hydroxypropyl Methylcellulose (3 cps) | 23.00 |

| Sr. No. | Ingredients | Qty (mg/cap) |
|---|---|---|
| 4 | Simethicone Emulsion | 0.415 |
| 5 | Purified water | qs |
| 6 | Sugar Spheres | 14.799 |
| 7 | Talc | 1.386 |
| Total weight | | 135.00 |

Brief Manufacturing Procedure
Step I. Nanonization of Fenofibrate:
1. Steadily add Hydroxypropyl Methylcellulose to purified water while stirring until to form a clear solution.
2. Add sodium lauryl sulphate (SLS) to the step-1 under constant stirring.
3. Add fenofibrate to the step-2 under constant stirring.
4. Add simethicone emulsion to the suspension of step 3 and stir slowly to form a uniform suspension.
5. Filter the suspension of step 4 through mesh #100 ASTM.
6. Pass the suspension of step 5 through DYNO MILL till the desired particle size is obtained.

Step II. Drug Loading:
7. Load the sugar spheres in the fluidized bed processor and pre warm to the product bed temperature of 40±5° C.
8. Spray the suspension of step 6 on the sugar spheres of step 7.
9. Sift the fenofibrate loaded pellets through mesh #14 ASTM.

Step III. Lubrication:
10. Sift talc through mesh #40 ASTM and mix with the pellets of step 9 by using suitable blender for 5 minutes for lubrication.

Step IV. Capsule Filling:
11. Fill the final pellets of step 10 into a suitable capsule shell. Alternatively, fill the final pellets of step 10 for 30 mg composition of fenofibrate in a capsule of suitable size.

Example 2

Composition Comprising Nanoparticulate & Micronized Fenofibrate in a Ratio of 75:25

| Sr. No. | Ingredients | Qty (mg/cap) |
|---|---|---|
| | Part A: Nanoparticulate Fenofibrate Suspension | |
| 1 | Fenofibrate (Nanonised) | 67.50 |
| 2 | Sodium lauryl sulphate | 5.40 |
| 3 | Hydroxypropyl Methylcellulose (3 cps) | 23.00 |
| 4 | Purified water | qs |
| | Part B | |
| 5 | Fenofibrate (Micronized) | 22.50 |
| 6 | Purified water | qs |
| 7 | Simethicone Emulsion | 0.415 |
| | Spray Granulation of Fenofibrate Suspension | |
| 7 | Sugar Spheres | 14.799 |
| | Lubrication | |
| 8 | Talc | 1.386 |
| Total weight | | 135.00 |

Brief Manufacturing Procedure
Step I. Preparation of Fenofibrate Suspension:
1. Steadily add Hydroxypropyl Methylcellulose to purified water while stirring until to form a clear solution.
2. Add sodium lauryl sulphate (SLS) to the step-1 under constant stirring.
3. Add fenofibrate to the step-2 under constant stirring.
4. Filter the suspension of step 3 through suitable sieve.

Step II. Nanonization of Fenofibrate Suspension:
5. Pass the drug suspension of step 4 through Dyno mill for sufficient no. of cycles to achieve desired particle size.
6. Filter the nanonised suspension of step 5 through suitable sieve.
7. Add fenofibrate (micronized) from part B to the suspension of step 6 under constant stirring.
8. Add simethicone emulsion to the suspension of step 7 and filter the suspension through suitable mesh.

Step II. Drug Loading:
9. Load the sugar spheres in the fluidized bed processor and pre warm to the product bed temperature of 40±5° C.
10. Spray the suspension of step 8 on the sugar spheres of step 9.
11. Dry the drug loaded pellets of step 10.

Step III. Lubrication:
12. Sift talc through mesh #40 ASTM and mix with the pellets of step 11 by using suitable blender for 5 minutes for lubrication.

Step IV. Capsule Filling:
13. Fill the final pellets of step 12 into a suitable capsule shell. Alternatively, fill the final pellets of step 12 for 30 mg composition of fenofibrate in a capsule of suitable size.

Example 3

Composition Comprising Nanoparticulate & Micronized Fenofibrate in a Ratio of 60:40

| Sr. No. | Ingredients | Qty (mg/cap) |
|---|---|---|
| 1 | Fenofibrate (Nanonised) | 54.00 |
| 2 | Fenofibrate (Micronized) | 36.00 |
| 3 | Sodium lauryl sulphate | 5.40 |
| 4 | Hydroxypropyl Methylcellulose (3 cps) | 23.00 |
| 5 | Simethicone Emulsion | 0.415 |
| 6 | Purified water | qs |
| 7 | Sugar Spheres | 14.799 |
| 8 | Talc | 1.386 |
| Total weight | | 135.00 |

Example 4

Composition Comprising Nanoparticulate & Micronized Fenofibrate in a Ratio of 50:50

| Sr. No. | Ingredients | Qty (mg/cap) |
|---|---|---|
| 1 | Fenofibrate (Nanonised) | 45.00 |
| 2 | Fenofibrate (Micronized) | 45.00 |
| 3 | Sodium lauryl sulphate | 5.40 |
| 4 | Hydroxypropyl Methylcellulose (3 cps) | 23.00 |
| 5 | Simethicone Emulsion | 0.415 |
| 6 | Purified water | qs |

-continued

| Sr. No. | Ingredients | Qty (mg/cap) |
|---|---|---|
| 7 | Sugar Spheres | 14.799 |
| 8 | Talc | 1.386 |
| Total weight | | 135.00 |

Example 5

Composition Comprising Nanoparticulate & Micronized Fenofibrate in a Ratio of 40:60

| Sr. No. | Ingredients | Qty (mg/cap) |
|---|---|---|
| 1 | Fenofibrate (Nanonised) | 36.00 |
| 2 | Fenofibrate (Micronized) | 54.00 |
| 3 | Sodium lauryl sulphate | 5.40 |
| 4 | Hydroxypropyl Methylcellulose (3 cps) | 23.00 |
| 5 | Simethicone Emulsion | 0.415 |
| 6 | Purified water | qs |
| 7 | Sugar Spheres | 14.799 |
| 8 | Talc | 1.386 |
| Total weight | | 135.00 |

Examples 3, 4 and 5 have also been prepared according to the manufacturing process as described for example 2.

We claim:

1. An oral pharmaceutical composition comprising fenofibrate, wherein the composition comprises a mixture of nanoparticulate fenofibrate and micronized fenofibrate and one or more pharmaceutically acceptable excipients, wherein the pharmaceutical composition is a solid, the ratio of the nanoparticulate fenofibrate to the micronized fenofibrate is 50:50 wt/wt, and the pharmaceutical composition includes a dosage of about 90 mg of fenofibrate, wherein the composition is bioequivalent to ANTARA® capsule containing 130 mg of micronized fenofibrate particles, wherein the bioequivalence of the composition is established by: (i) a 90% Confidence Interval for AUC which is between 0.80 and 1.25; and (ii) a 90% Confidence Interval for CmnaX, which is between 0.80 and 1.25 under fasting condition.

2. The pharmaceutical composition of claim 1 which is substantially free of food effect.

3. The pharmaceutical composition of claim 1 wherein the composition is formulated into a dosage form selected from the group consisting of tablets and capsules.

4. The pharmaceutical composition of claim 1, wherein nanoparticulate fenofibrate has an effective particle size of about 1 nm to about 950 nm.

5. The pharmaceutical composition of claim 1, wherein micronized fenofibrate has an effective particle size of about 1 μm to about 50 μm.

6. A method of treating a patient for primary hyperlipidemia, hypercholesterolemia, and/or hypertriglyceridemia comprising administering to the patient in need thereof an effective amount of the pharmaceutical composition of claim 1.

* * * * *